(12) United States Patent
Liu et al.

(10) Patent No.: US 7,659,308 B2
(45) Date of Patent: Feb. 9, 2010

(54) CONCENTRICOLIDE AND ITS DERIVATIVES, PROCESS FOR PREPARING THEM, PHARMACEUTICAL COMPOSITION COMPRISING THE SAME AND ITS USE

(75) Inventors: Jikai Liu, Kunming (CN); Yongtang Zheng, Kunming (CN); Xiangdong Qin, Kunming (CN); Liumeng Yang, Kunming (CN); Zejun Dong, Kunming (CN); Ruirui Wang, Kunming (CN); Jianwen Tan, Kunming (CN)

(73) Assignees: Kunming Institute of Botany, The Chinese Academy of Sciences, Kunming (CN); Kunming Institute of Zoology, The Chinese Academy of Sciences, Kunming (CN)

( * ) Notice: Subject to any disclaimer, the term of this patent is extended or adjusted under 35 U.S.C. 154(b) by 291 days.

(21) Appl. No.: 10/576,758

(22) PCT Filed: Oct. 20, 2004

(86) PCT No.: PCT/CN2004/001188

§ 371 (c)(1),
(2), (4) Date: Mar. 5, 2007

(87) PCT Pub. No.: WO2005/137841

PCT Pub. Date: Apr. 28, 2005

(65) Prior Publication Data

US 2007/0155830 A1   Jul. 5, 2007

(30) Foreign Application Priority Data

Oct. 22, 2003   (CN) .................. 2003 1 0110784

(51) Int. Cl.
*A61K 31/34* (2006.01)
*C07D 307/00* (2006.01)
(52) U.S. Cl. ..................... 514/468; 549/299
(58) Field of Classification Search ............. 549/299; 514/468
See application file for complete search history.

(56) References Cited

OTHER PUBLICATIONS

Murray et al DN 106:101992 (1986) abstract.*
Padwa et al DN 138:170018 (2003) abstract.*

* cited by examiner

*Primary Examiner*—Janet L. Andres
*Assistant Examiner*—Raymond Covington
(74) *Attorney, Agent, or Firm*—Seed IP Law Group PLLC

(57) ABSTRACT

The present invention relates to concentricolide and its derivatives, a method for the preparation of the compound and its derivatives, a pharmaceutical composition containing concentricolide and its derivatives, and use of the compound and its derivatives for the treatment and prevention of infection caused by human immunodeficiency virus (HIV).

8 Claims, 4 Drawing Sheets

CONCENTRICOLIDE AND ITS DERIVATIVES, PROCESS FOR PREPARING THEM, PHARMACEUTICAL COMPOSITION COMPRISING THE SAME AND ITS USE

TECHNICAL FIELD

The invention relates to concentricolide and its derivatives, a process for preparing the compound and its derivatives, a pharmaceutical composition comprising concentricolide and its derivatives, and use of the compound and its derivatives for the treatment and prevention of the infection caused by human immunodeficiency virus (HIV).

BACKGROUND ART

Fungi of ascomycete genus *Daldinia* and other Xylariaceae are rich in unique secondary metabolites. European and American *Daldinia* sp. have been studied by Allport and Bu'Lock (D. C. Allport, J. D. Bulock, *J. Chem. Soc.*, 1958, 4090; D. C. Allport, J. D. Bulock, *J. Chem. Soc.*, 1960, 654.) and Anke et al., (H. Anke, M. Stadler, A. Mayer, O. Sterner, *Can. J. Bot.*, 1995, 73, 802), respectively, thereby resulted in the identification of characteristic metabolites in their stromata and cultures. Recently, two Japanese *Daldinia* sp. have been investigated intensively by Hashimoto and Asakawa (M. Stadler, H. Wollweber, A. Muhlbauer, T. Henkel, Y. Asakawa, T. Hashimoto, Y. M. Ju, J. D. Rogers, H. G. Wetzstein, H. W. Tichy, *Mycotaxon* 2001, 77, 379; M. S. Buchanan, T. Hashimoto, S. Takaoka, et al., *Phytochemstry* 1996, 42, 173; D. N. Quang, T. Hashimoto, M. Tanaka, M. Baumgartner, M. Stadler, Y. Asakawa. *Phytochemstry* 2002, 61, 345; M. Buchanan, T. Hashimoto, and Y. Asakawa, *Phytochemstry* 1995, 40, 135; M. S. Buchanan, T. Hashimoto, and Y Asakawa, *Phytochemstry* 1996, 41, 821.5-9). More than 20 new metabolites have been discovered, and some of these compounds exhibit a wide range of biological activities including antimicrobial and nematicidal activities.

SUMMARY OF THE INVENTION

The inventor has discovered a novel compound having benzonfuran lactone as backbone from Chinese *Daldinia concentrica* collected at Lijiang of Yunnan, which compound is named concentricolide A.

The concentricolide exhibits good antifusion biological activity. It can prevent HIV to enter into normal cells, inhibit the reproduction of HIV and delay the destruction of human immune system. Accordingly, the concentricolide can be used for prevention and/treatment of HIV infection.

The invention at first aspect relates to compounds of the general formula (I) or derivatives thereof

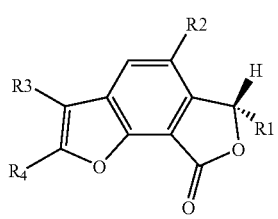

(I)

In which
R1 represents $C_1$-$C_4$ alkyl;
R2 represents H, halogen, —OH, NRR' or —$NO_2$, wherein R and R' represent H or $C_1$-$C_6$ alkyl;
R3 represents H, halogen, —OH, NRR' or —$NO_2$, wherein R and R' represent H or $C_1$-$C_6$ alkyl;
R4 represents H, halogen or —$NO_2$.

The invention at another aspect relates to a pharmaceutical composition comprising, as active ingredients, the compounds of the general formula (I) or derivatives thereof and pharmaceutically acceptable carriers or excipients.

The invention also relates to a process for preparing the compounds of the general formula (I) or its derivatives, comprising:
a) extracting the fruiting body of *Daldinia concentrica* from Yunnan or its fermented liquid with an organic solvent;
b) separating the extract by silica gel column chromatography to give the compound of the formula (II):

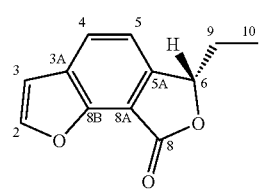

(II)

c) subjecting the compound of the formula (II) to bromination, nitration or alkylation to give the compound of the formula (I).

The invention also relates to the use of the compounds of formula (I) for the manufacture of a medicament for the treatment/prevention of the conditions or diseases associated with HIV infection.

The invention further relates to a method for the prevention/treatment of conditions or diseases associated with HIV infection, comprising administrating the compound of the formula (I) or its derivatives to a patient infected by HIV.

The invention further relates to an extract of *Daldinia concentrica* from Yunnan, characterized in that the extract contains a compound of formula (II)

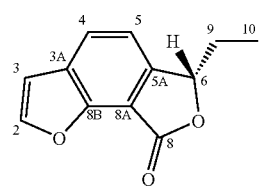

(II)

The invention further relates to a pharmaceutical composition comprising, as active ingredients, an extract of *Daldinia concentrica* and pharmaceutically acceptable carriers or excipients, in which the extract of *Daldinia concentrica* contains concentricolide of the formula (II).

The invention further relates to the use of the extract of *Daldinia concentrica* for the preparation of a product for the prevention/treatment of conditions or diseases associated with HIV infection.

According to the invention, the compound of formula (I) or its derivatives are selected preferably from the compounds represented by the following formulae:

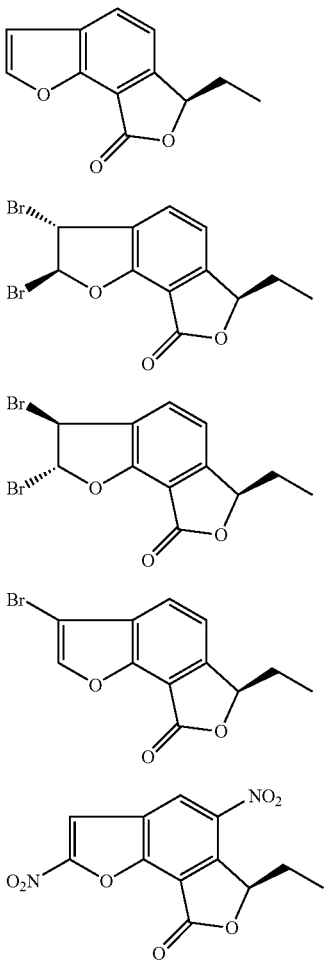

more preferably from the compound of formula (II).

According to the invention, the compound of formula (I) or its derivatives comprise optical stereoisomers thereof, preferably a stereoisomer represented by the formula (II).

According to the invention, the term "derivatives of a compound of formula (I)" means pharmaceutically acceptable salts, stereoisomers, hydrates or solvates of the compound of formula (I).

According to the invention, the compounds concerned in this invention form salts with a variety of organic and inorganic acids, including physiologically acceptable salts which are commonly used in pharmaceutical chemistry. Such salts are also included in this invention. Examples of typical inorganic acids used to form such salts include hydrochloric acid, nitric acid, sulfuric acid, phosphoric acid and the like. Examples of typical organic acids include: mono- and bi-aliphatic acids, phenyl substituted alkanoic acids, hydroxyalkanoic acids and hydroxyalkandioic acids, aromatic acids, aliphatic and aromatic sulfonic acids and so on. The pharmaceutically acceptable salts include acetates, phenylacetates, trifluoroacetates, acrylates, ascorbates, benoates, chlorobenzoates, ldinitrobenoates, hydroxybenzoates, methoxybenzoates, methylbenzoates, O-acetoxybenzoates, naphthalene-2-benzoates, bromides, isobytyrates, phenylbutyrates, β-hydroxybutyrates, butyne-1,4-dioates, hexyne-1,4-dioates, caprates, caprylates, chlorides, cinnamates, citrates, formates, fumarates, glycollates, heptanoates, hippurates, lactates, malates, maleates, hydroxymaleates, malonates, mandelates, mesylates, nicotinates, isonicotinates, nitrates, oxalates, phthalates, teraphthalates, phosphates, monohydrogenphosphates, dihydrogenphosphates, metaphosphates, pyrophosphates, propiolates, propionates, phenylpropionates, salicylates, sebacates, succinates, suberates, sulfates, bisulfates, pyrosulfates, sulfites, bisulfites, sulfonates, benzene-sulfonates, p-bromophenylsulfonates, chlorobenzene-sulfonates, ethanesulfonates, 2-hydroxyethanesulfonates, methanesulfonates, naphthalene-1-sulfonates, naphthalene-2-sulfonates, p-toluenesulfonates, xylenesulfonates, tartarates and the like. The preferred salt is hydrochlorides.

According to the invention, the compound of the formula (II) is prepared from fungus material of *Daldinia* sp. The comminuted fungus material of *Daldinia* sp. is extracted with an organic solvent (e.g. methanol, ethanol, propanol, isopropanol, acetone, ethyl acetate, chloroform, diethyl ether, t-butyl methyl ether, tetrahydrofuran, acetonitrile), the extract is concentrated and adsorbed on a solid carrier. The solid carrier includes ground natural ores (e.g. kaolin, clay, talc, chalk, quartz, montmorillonite) and ground synthetic minerals (e.g. silica, alumina, silicates) or absorber resins (e.g. phenol-formaldehyde resins or polyamide resins). The absorbed extract is subjected to gradient elution using mixed solvents of increasing polarity, the eluent is concentrated and further purified on silica gel column.

Alternatively, the compound of formula (II) is prepared by extracting the fermented liquid cultures of *Daldinia concentrica* with an organic solvent (e.g. ethyl acetate, diethyl ether, chloroform, methylene chloride, butanol), concentrating the extract and absorbing on a solid carrier including ground natural minerals (e.g. kaolin, clay, talc, chalk, quartz, montmorillonite) and ground synthetic minerals (e.g. silica, alumina, silicates) or absorber resins (e.g. phenol-formaldehyde resins or polyamide resins), subjecting the absorbed extract to gradient elution, concentrating the eluent and purifying on silica gel column.

According to the invention, the compounds of the formula (I) or (II) are suitable for the treatment of acquired immunodeficiency syndrome (AIDS) caused by the infection of human immunodeficiency virus (HIV). The compounds can be isolated directly from fungi or be obtained by full synthesis or semi-synthesis. All the compounds according to the invention are used separately or in the form of pharmaceutical composition when they are used for treating the infection caused by human immunodeficiency virus (HIV). The invention also concerns to the use of extracts of *Daldinia* sp. for the treatment of the infection caused by human immunodeficiency virus (HIV). The extracts comprise the compound of formula (II) and can be used in combination with other compounds or formulations which are suitable for the treatment of the infection caused by HIV.

Further, the extracts of *Daldinia* sp. can be obtained by conventional extraction steps using above organic solvents. The extracts of various purity grades can be used. The content of the compound of the formula (II) in the extract is in the range of 0.01 to 2% be weight, preferably in the range of 0.1 to 1% by weight.

The invention also relates to the use of fungi of *Daldinia* sp. for the treatment of the infection caused by human immunodeficiency virus (HIV). The fungi is preferably in. the form of comminuted fruiting bodies or stromata and cultures. The comminuted fungus can be used together with other compounds or formulations for the treatment of the infection caused by HIV.

One or more compounds of formula (I) or (II) are compressed together with excipients, diluents or carriers into tables or other oral dosage forms, or formulated as pharmaceutical dosage forms for intramuscular or intravenous injection, or as sustained release dosage forms and the like.

Pharmaceutical formulations are prepared by procedures known in the art. In particular, the compounds according to the invention can be formulated with common excipients, diluents or carriers, and formed into tablets, capsules, suspensions, powders and the like. Examples of excipients, diluents and carriers include fillers and extenders (such as starch, sugars, mannitol, and silicic derivatives), binding agents (such as carboxymethyl cellulose, other cellulose derivatives, alginates, gelatin, and polyvinyl pyrrolidone), moisturizing agents (such as glycerol), slow release agents (such as paraffin), resorption accelerators (such as quaternary ammonium salts), surfactants (such as cetyl alcohol, glycerol monostearate), adsorptive carriers (such as kaolin and bentonite) and lubricants (such as talc, calcium stearate, magnesium stearate, and solid polyethyl glycols).

The compounds according to the invention can be formulated as non-oral dosage forms, such as the dosage forms for intramuscular, subcutaneous or intravenous injections, or as sustained release dosage forms and the like. The formulations can be so constituted that they release the active ingredient in a particular part of the intestinal tract over a period of time. The coatings, envelopes, and protective matrices may be made from polymeric materials or waxes.

The particular dosage of the compound of formula (I) or (II) for the treatment of the infection caused by the human immunodeficiency virus (HIV) is dependent upon many factors, such as the severity of diseases, body weight, age, sex, administration path, and specific diagnosis of clinician. Generally, accepted and effective daily doses are from 0.1 to 1000 mg/person/day, preferably from 50 to 200 mg/person/day. Such dosages are administered once to three times each day.

EMBODIMENTS

Figure 1:
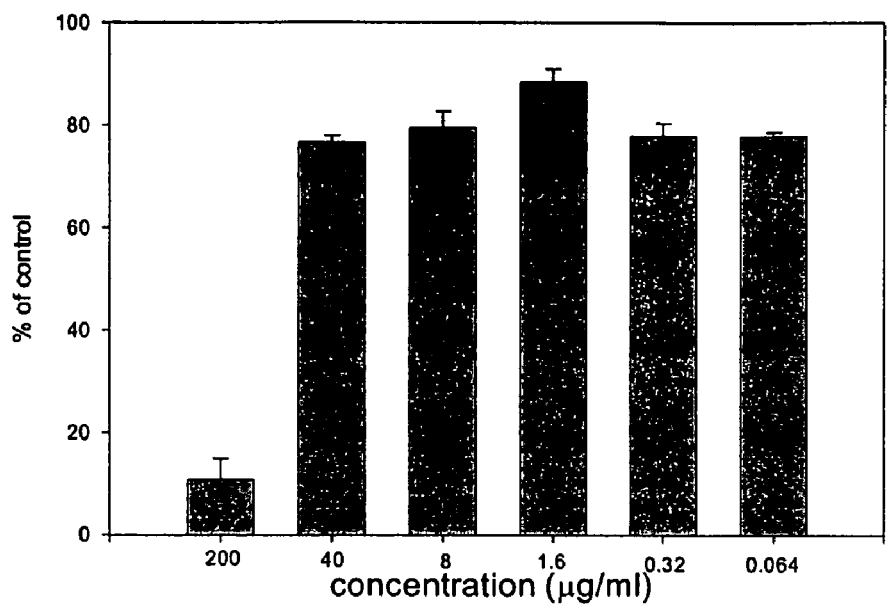
FIG. 1 The cytotoxicity of concentricolide A or II on C8166 cells ($CC_{50}$ is 76.66 μg/ml)

Following examples are used to further describe the invention, but do not limit the invention at any way.

EXAMPLE 1

Preparation of Concentricolide A

Dried and comminuted fruiting bodies (750 g) of *Daldinia concentrica* were extracted for three times with $CHCl_3$—MeOH (1:1, vol/vol) and MeOH at room temperature, respectively. The organic phase was combined and evaporated in vacuo to give a deep brown and cream crude extract (60 g).

The extract was mixed with 80-100 mesh silica gel and submitted to silica gel chromatography eluting successively with $CHCl_3$/MeOH (100:0, 95:5, 90:10, vol/vol) to give 15 fractions. The fraction 8 (eluted with $CHCl_3$/MeOH, 95:5, 9 g) was subjected to silica gel chromatography eluting successively with petroleum ether/acetone (99:1, 95:5, 90:10, 80:20, |vol/vol|). From the fraction eluted with 99:1 petroleum ether/acetone was directly obtained 120 mg concentricolide A.

Alternatively, the liquid culture (80 L) of *Daldinia concentrica* was extracted for five times with EtOAc at room temperature. The combined organic phase was evaporated in vacuo to give a deep brown and cream crude extract (24 g). The crude extract was mixed with 80-100 mesh silica gel and submitted to silica gel chromatography eluting with $CHCl_3$/MeOH (100:0, 95:5, 90:10, vol/vol) to give 15 fractions. The fraction 8 (obtained by eluting with $CHCl_3$/MeOH, 95:5, 1.7 g) was subjected to gel chromatography eluting with petroleum ether/acetone (99:1, 95:5, 90:10, 80:20, |vol/vol|). From the fraction eluted with 99:1 petroleum ether/acetone was directly obtained 173 mg concentricolide A.

Concentricolide A has the following physico-chemical and wave spectrum date: pale yellow needles, m.p. 89~90° C. (petroleum ether-acetone); $[\alpha]_D^{21.9}=-59.23°$ (c 0.48, MeOH); EI-MS m/z (rel. int.): 202 $[M]^+$(20), 173 (100), 145 (48); HR-TOF-MS m/z: 225.0526 ($[M+Na]^+$, 225.0527 calcd. for $C_{12}H_{10}O_3Na$); UV(MeOH)$\lambda_{max}$ nm: 226 (log ∊ 4.08), 256.5 (3.88), 297 (3.63); IR $\nu_{max}^{KBr}cm^{-1}$: 1757, 1641, 1534, 1437.

$^1$H- and $^{13}$C-NMR data of concentricolide (500 MHz, $CD_3OD$, δ in ppm, J in Hz)

| | δ (C)(DEPT) | Δ (H) | $^1$H-$^1$HCOSY | HMBC (selected) |
|---|---|---|---|---|
| CH (2) | 146.4(CH) | 7.74(1H, d, J=2.2) | H-3 | H-3 |
| CH (3) | 106.6(CH) | 6.86(1H, d, J=2.2) | H-2 | H-2, 4 |
| C (3A) | 128.9(C) | | | H-2, 5 |
| CH (4) | 127.8(CH) | 7.86(1H, d, J=8.3) | H-5 | H-3 |
| CH (5) | 116.0(CH) | 7.24(1H, d, J=8.3) | H-4 | |
| C (5A) | 147.8(C) | | | H-4, 9 |
| CH (6) | 82.9(CH) | 5.52(1H, dd, J=7.1, 4.1) | H-9a | H-5, 9, 10 |
| C (8B) | 110.9(C) | | | H-5, 6 |
| C (8B) | 149.6(C) | | | H-2, 3, 4 |
| $CH_2$ (9) | 27.8($CH_2$) | 1.81(1H, m) | H-6, 9b, 10 | H-6, 10 |
| | | 2.13(1H, m) | H-9a, 10 | |
| $CH_3$ (10) | 8.7($CH_3$) | 0.95(3H, t, J=7.2) | H-9a, 9b | H-6, 9 |
| C (8) | 168.9(C) | | | H-6 |

Figure 7:
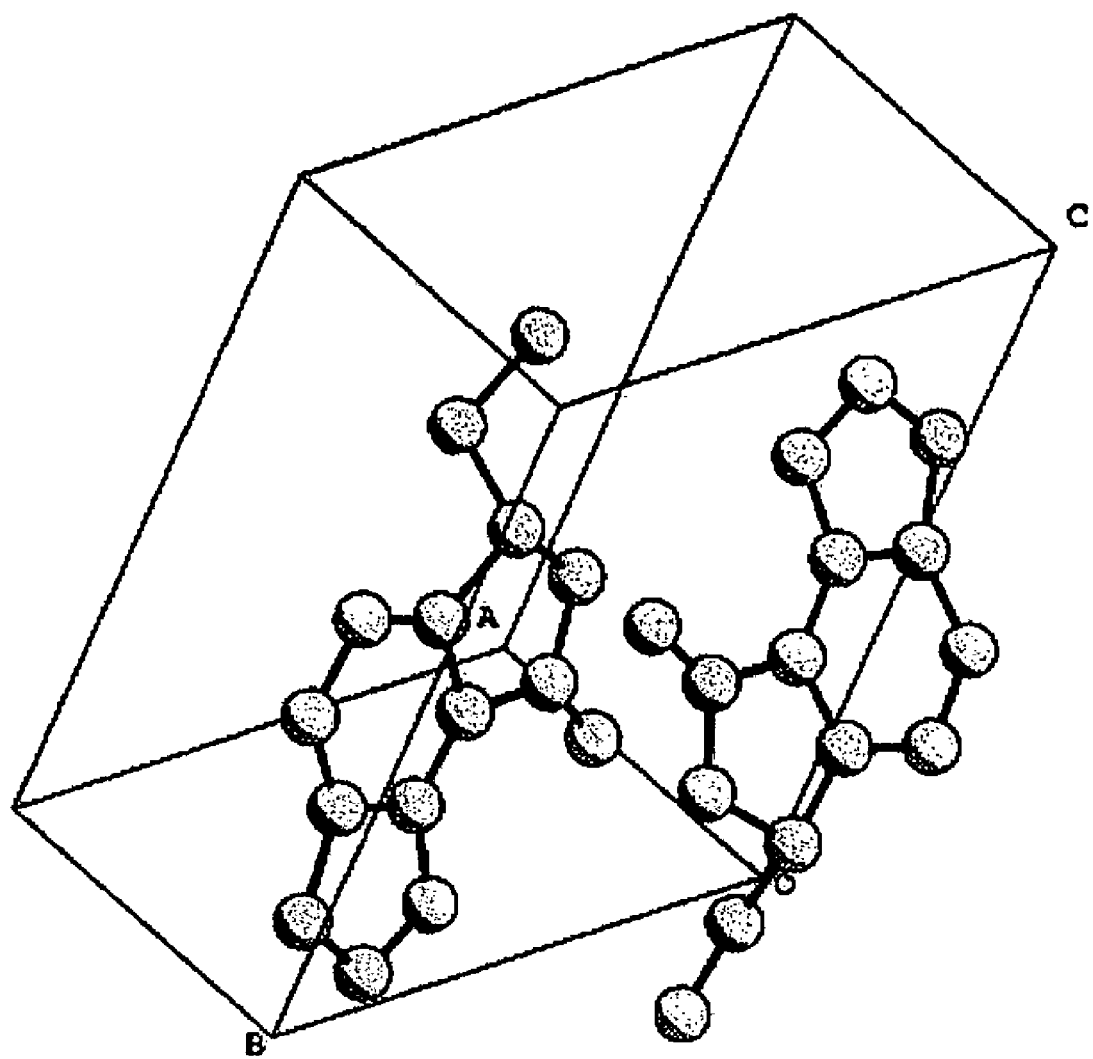
FIG. 7 Lattice diffraction pattern of concentricolide A according to the invention.

X-Ray Diffraction Analysis Results:

$C_{12}H_{10}O_3$, M 202, triclinic, space group P1; a=7.728(1), b=8.289(1), c=9.043(1) Å; α=106.450(5)°, β=96.321(6)°, γ=108.946(6)°; V=512.36(3) Å$^3$, Z=2. Final reliable factor $R_f$=0.073 and $R_w$=0.066 (w=1/σ $|F|^2$). A total of 1369 reflections were recorded in the ω scanning mode with a MAC-DIP-2030K diffractometer with graphite-monochromated MoKα scanning radiation. The structure was solved by the direct method SHELXS86. Its lattice diffraction pattern was shown in FIG. 7.

EXAMPLE 2

The preparation of 2,3-dibromo-2,3-dihydroconcentricolide (B) from concentricolide A 60 mg of concentricolide (A, 0.30 mmol) was dissolved in 2 ml $CHCl_3$, 65 mg bromine (0.41 mmol) was dissolved in 1 ml $CHCl_3$. The bromine solution was added dropwise to the solution of A and stirred at room temperature for 120 hours. The product was concentrated to give pale yellow needles, which was recrystallized to obtain 50.8 mg of B with a yield of 47.2%. The product showed two peaks on HPLC which are identified to be a pair of optical isomers ($B_1$ and $B_2$).

Pale yellow needle compound B was produced by addition reaction of concentricolide A and bromine. EI-MS spectrum showed three isotope peaks at 364, 362 and 360 with a relative intense of 1:2:1, indicating that the molecular contains two atoms. By comparison with concentricolide A, there is just the difference of molecular weight of two bromine atoms, further proving the existence of two bromine atoms. In $^1$H-NMR spectrum, two olefinic hydrogen coupled each other [δ 7.79 (1H, d, J=7.7), 7.19 (1H, d, J=7.7)] was observed. Based on coupling constant J=7.7, it is inferred to be hydrogen on the phenyl ring, suggesting the bromine addition reaction occurred at the position 2 and 3. In HMBC, $δ_H$ 7.79 was related to C-3, 5A and 8A, and $δ_H$ 7.19 was related to C-3A, 4, 5A and 8A, which further proved that the addition reaction occurred at furan ring. Therefore, the structure of B was determined to be 2,3-dibromine omo-2,3-hydroconcentricolide. HPLC of B showed that there are two peaks, because bromine addition reaction was bromine onium ion mechanism, two bromine atoms took contrary directions to attack the olefinic carbon. The product of the addition reaction should be a pair of optical isomers, that is, B was indeed a mixture, in which the structures of the two compounds were (2S,3S)-2,3-dibromo-2,3-hydroconcentricolide ($B_1$) and (2R,3R)-2,3-dibromo-2,3-hydroconcentricolide ($B_2$), respectively.

2,3-Dibromo-2,3-dihydroconcentricolide ($B_1$ and $B_2$). Pale yellow needles (petroleum ether/acetone)

EI-MS m/z (rel. int.): 364 $[M_1]^+$ (0.5), 362$[M_2]^+$ (1.0), 360$[M_3]^+$ (0.5), 284(7), 282 (13), 280 (31), 278 (7), 202 (20), 173 (100), 145 (50), 117 (7), 89 (12);

$^1$H-NMR (500 MHz, $CDCl_3$): δ7.79 (1H, d, J=7.7), 7.19 (1H, d, J=7.7), 7.02 (1H, d, J=3.8), 5.79 (1H, d, J=4.2), 5.46 (1H, m), 2.14 (1H, m), 1.86 (1H, m), 1.06 (3H, t, J=7.4);

$^{13}$C-NMR (100 MHz, $CDCl_3$): δ 166.6, 166.6, 153.9, 153.9, 153.8, 153.8, 131.6, 131.5, 128.1, 128.0, 117.1, 117.1, 112.2, 112.0, 90.1, 90.0, 82.8, 82.8, 50.9, 50.8, 27.8, 27.7, 9.1, 9.0.

EXAMPLE 3

The preparation of 3-bromoconcentricolide (C) from 2,3-dibromo-2,3-dihydroconcentricolide (B)

32 mg B (0.09 mmol) was dissolved in 2 ml methanol, to the solution was added 1 ml saturated methanol solution of potassium hydroxide. The mixture was stirred at room temperature for 8 hr. The reaction solution was neutralized to pH 7.0 with 1% hydrochloric acid in methanol and diluted with a small amount of water and extracted with chloroform. The extract was dried to obtain a crude product. The crude product was recrystallized to give 11.8 mg pale yellow needles C with a yield of 47.5%.

Pale yellow needles compound C was obtained as an elimination reaction product of B. EI-MS spectrum showed two molecular ion peaks at 282 and 280 with a relative intense of 1:1, indicating the existence of one bromine atom. Three olefinic hydrogen signals [δ 7.84 (1H, d, J=8.0), 7.80 (1H, s), 7.34 (1H, d, J=8.0)] were observed in $^1$H-NMR. Comparing the signals with those of A [δ 7.74 (1H, d, J=2.2, H-2), 6.86 (1H, d, J=2.2, H-3), 7.86 (1H, dd, J=8.3, 3.6, H-4), 7.24 (1H, d, J=8.3, H-5)], the eliminated was H-3. HMBC showed that there were relevant peaks of $δ_H$ 7.80(1H, s) and C-3, 3A, 8B, further proving that the structure of the compound was 3-bromoconcentricolide.

3-Bromoconcentricolide (C). Pale yellow needles(petroleum ether/acetone); m.p. 88~89.5° C.; EI-MS m/z (rel. int.): 282 $[M_1]^+$ (20), 280 $[M_2]^+$ (21), 253 $[M_1-C_2H_5]^+$ (80), 251 $[M_2-C_2H_5]^+$ (100), 225 (52), 223 (68); $^1$H-NMR (400 MHz, $CDCl_3$): δ7.84 (1H, d, J=8.0), 7.80 (1H, s), 7.34 (1H, d, J=8.0), 5.56 (1H, m), 2.18 (1H, m), 1.84 (1H, m), 0.99 (3H, t, J=7.4); $^{13}$C-NMR (100 MHz, $CDCl_3$): δ 167.2, 149.5, 149.2, 144.1, 128.8, 126.5, 116.8, 111.6, 98.3, 82.9, 27.8, 8.7; 2D-NMR.

EXAMPLE 4

The preparation of 2,5-dinitroconcentricolide (D) from concentricolide A 50 mg A (0.25 mmol) was dissolved in 1 ml $CHCl_3$, to the solution was added 1.5 ml thick sulphuric acid at cooling condition and added dropwise 1 ml thick nitric acid with stirring. The mixture was stirred at room temperature for 30 minutes and then poured onto smashed ice. Remained acid was removed by using sodium carbonate. The mixture was diluted with a small amount of water and extracted with chloroform. The extract was dried to obtain a crude product, which was recrystallized to give 31.8 mg pale yellow needles D, with a yield of 44%.

2,5-Dinitroconcentricolide (D). Pale yellow needles (petroleum ether/acetone); m.p. 203~205° C.; EI-MS m/z (rel. int.): 292 $[M]^+$ (25), 263 $[M-C_2H_5]^+$ (100); HR-TOF-MS m/z: $C_{12}H_8N_2O_7$ ($[M+Na]^-$ 315.0220, cal. for $C_{12}H_8N_2O_7Na$ 315.0229); $^1$H-NMR (400 MHz, $CDCl_3$): δ8.98 (1H, s), 7.96 (1H, s), 6.13 (1H, m), 2.29 (1H, m), 1.77 (1H, m), 0.91 (3H, t, J=7.4); $^{13}$C-NMR(100 MHz, $CDCl_3$): δ 163.9, 155.3, 149.7, 147.1, 140.9, 128.2, 126.8, 114.6, 106.9, 84.1, 26.3, 9.1.

In the formulations, "active ingredient" means a compound of formula (I) or (II).

EXAMPLE 5

Gelatin Capsules

Hard gelatin capsules were prepared using the following methods:

| Composition | Quantity (mg/capsule) |
| --- | --- |
| Active ingredient | 0.1-1000 |
| Starch | 0-650 |
| flowable starch | 0-650 |
| Silicone fluid (350 centistokes) | 0-15 |

The ingredients were blended, passed through a sieve, and filled into hard gelatin capsules.

EXAMPLE 6

Concentricolide Capsule

| Composition | Quantity (mg/capsule) |
| --- | --- |
| Concentricolide | 100 |
| Starch | 100 |
| flowable Starch | 397 |
| Silicone fluid (350 centistokes) | 3 |

EXAMPLE 7

Tablets

| Composition | Quantity (mg/capsule) |
| --- | --- |
| Active ingredient | 0.1-1000 |
| Microcrystalline cellulose, | 0-650 |
| Silica | 0-650 |
| Stearate acid | 0-15 |

The above components were blended and compressed into tablets.

Tablets each containing 0.1-1000 mg of active ingredient were made up as follows:

EXAMPLE 8

Tablets

| Composition | Quantity (mg/tablet) |
| --- | --- |
| Active ingredient | 0.1-1000 |
| Starch | 45 |
| Microcrystalline cellulose | 35 |
| Polyvinylpyrrolidone (10% aqueous solution) | 4 |
| Carboxymethylcellulose sodium | 4.5 |
| Magnesium stearate | 0.5 |
| Talc | 1 |

The active ingredient, starch, and cellulose were passed through a sieve and mixed. To the mixture was added polyvinylpyrrolidone to form a solution. The solution was passed through a sieve to produce pharmaceutical granules. The granules were dried at 50-60° C. and passed through a sieve. The carboxymethylcellulose sodium and magnesium stearate which passed through a sieve were mixed and compressed into tablets.

Suspensions each containing 0.1-1000 mg of effective ingredient per 5 ml dose were made as follows:

EXAMPLE 9

Suspensions

| Composition | Quantity (mg/5 ml) |
| --- | --- |
| Active ingredient | 0.1-1000 |
| Carboxymethylcellulose sodium | 50 |
| Syrup | 1.25 mg |
| Benzoic acid solution | 0.1 ml |
| Flavoring agent | q.v. |
| Colorant | q.v. |
| purified water | balanced up to 5 ml |

The effective ingredient was passed through a sieve and mixed with carboxymethylcellulose sodium and syrup to form a uniform paste. The benzoic acid solution, flavoring agent and colorant were diluted using water with stirring and then added the pharmaceutical paste, and balanced with water to the required volume.

Biological Activity Assay

Materials and Methods

Reagents and Chemicals

MTT (3, (4,5-dimethylthiazol-2-yl)-2,5-diphenyltetrazolium bromide) was purchased from Amresco; SDS (sodium dodecyl sulfate) was purchased from Serva; AZT (3P-azido-3P-deoxythymidine) was purchased from Sigma; DMF (N, N'-Dimethyl formamine ) was purchased from Shanghai Chemical Reagents Company (China).

Culture Medium

Complete RPMI-1640 medium supplemented with 10% fetal calf serum (Gibco), 2 mML-Glutamine, 10 Mm HEPES, 50 μM 2-Mercaptoethanol, 100,000 IU Penicillin, 100 μg/ml Streptomyces sulfate Compounds The testing compound was concentricolide A. The positive control: AZT, one of reverse transcriptase inhibitors, and T20, one of fusion inhibitors were used.

Cells and Virus

C8166 and HIV-1$_{IIIB}$ chronically infected H9 cells were donated by Medical Research Council (MRC), AIDS Reagent Project, UK. All cells and virus were stored and resuscitated by common methods.

EXAMPLE 1

The Cytotoxicity of Concentricolide A on C8166 Cells

C8166 was one of the host cells for HIV-1. 100 μl of 4×10$^5$/ml cells were seeded on microtiter plate, 100 μl of various concentrations of concentricolide were added and incubated at 37° C. in a humidified atmosphere of 5% $CO_2$ for 72 h. The cellular toxicity was assessed by MTT calorimetric assay. The plates were read on Bio-Tek ELx 800 ELISA reader at 595/630 nm ($OD_{595/630\ nm}$). 50% cytotoxic concentration ($CC_{50}$) was calculated as follows:

Cell viability %=$(OD_{exp}-OD_{blank})/(OD_{control}-OD_{blank})\times 100$.

Figure 2:
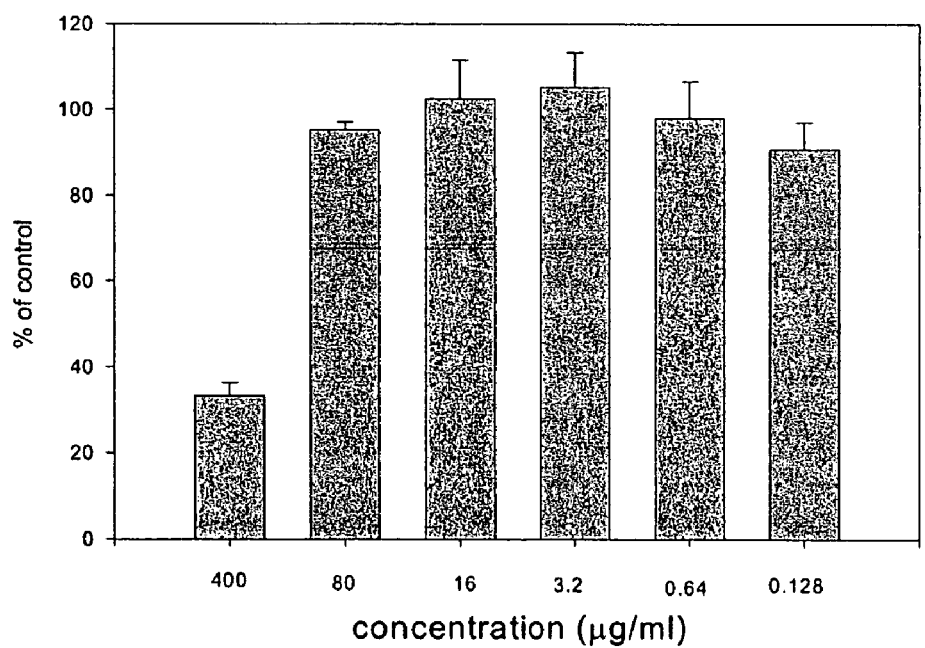
FIG. 2 The cytotoxicity of AZT on C8166 cells ($CC_{50}$ is 258.88 μg/ml)

The results were shown in FIGS. 1 and 2.

EXAMPLE 2

Figure 3:
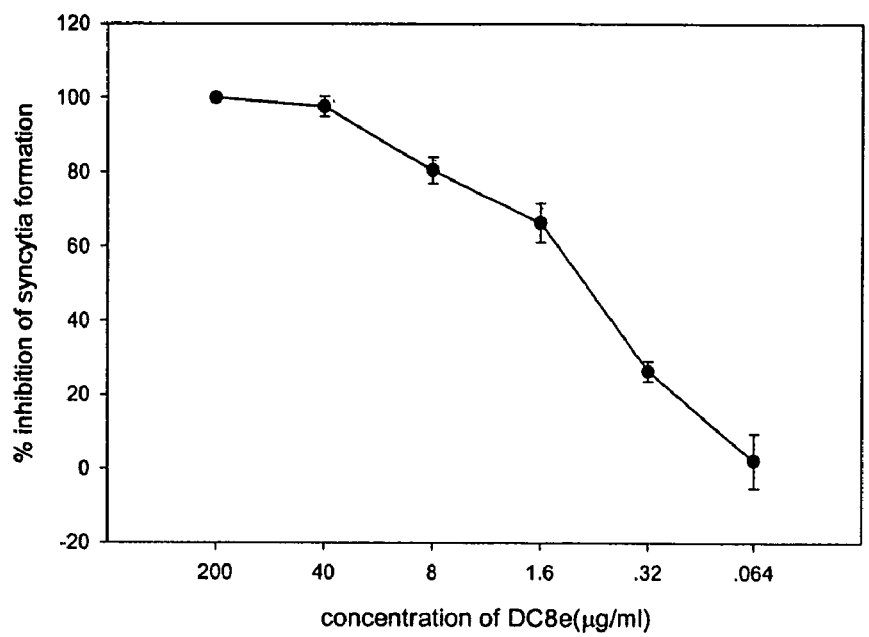
FIG. 3 The blockage of concentricolide A or II on binding and fusion between HIV-1 and cells ($EC_{50}$ is 0.83 μg/ml)
Figure 4:
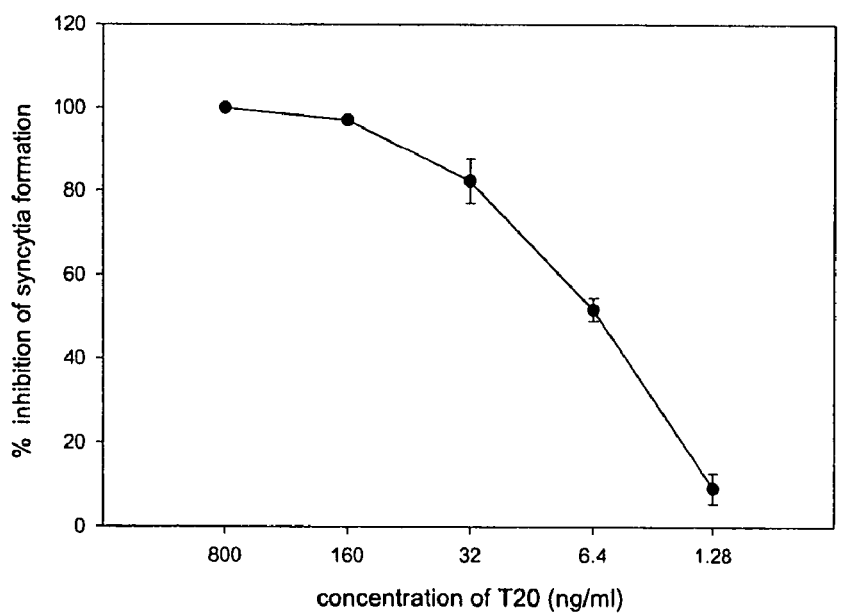
FIG. 4 The blockage of T20 on fusion of HIV-1 infected cells ($EC_{50}$ is 6.02 ng/ml)

The Blockage of Concentricolide A on Fusion Between Normal Cells and HIV-1 Infected Cells When HIV infected cells were co-cultured with normal T lymphocyte cells, the exterior envelope glycoprotein gp120 expressed on infected cells was bound to the cellular CD4 receptor of the uninfected $CD4^+$ cells, following fusion of cells and formation of syncytia. Compounds target to this site would inhibit the syncytia formation. Thus, this method could be used to detect whether the compounds have effect on binding and fusion between virus and host cell. Concentricolide A in example 1 was diluted by five fold on 96-well microtiter plate, 3 repeated wells in each gradient, 100 μl per well. Negative control well free of compounds and T-20 positive control well were set up. Then, 50 μl of C8166 cells at logarithmic growth period ($6\times10^5$/ml) and 50 μl of HIV-1 chronically infected H9 cells ($2\times10^5$/ml) were added in each well. The plate was cultured in a humidified incubator at 37° C. and 5% $CO_2$ for 24 h, and the syncytial formation was observed under microscope to deduce whether Concentricolide A blocks the fusion process of virus and cell. The results were as shown in FIGS. 3 and 4.

EXAMPLE 3

Figure 5:
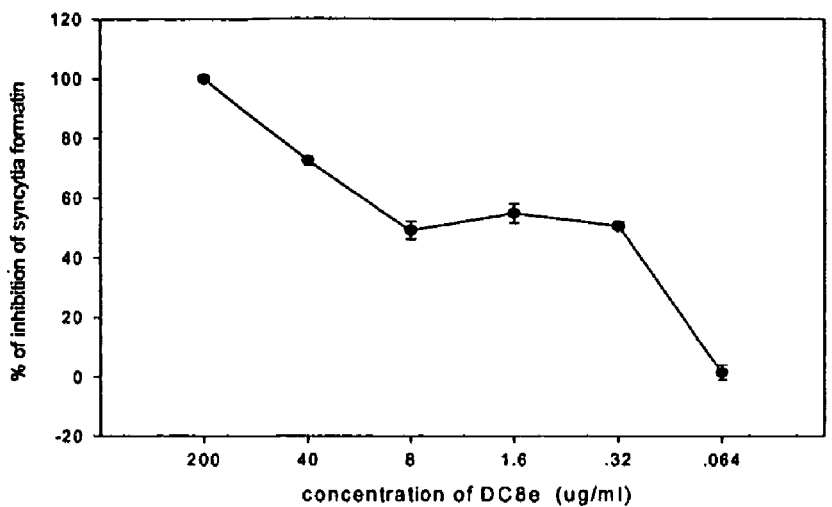
FIG. 5 Inhibition of concentricolide A or II on cytopathic effect (CPE) of HIV-1 ($EC_{50}$ is 0.31 μg/ml)
Figure 6:
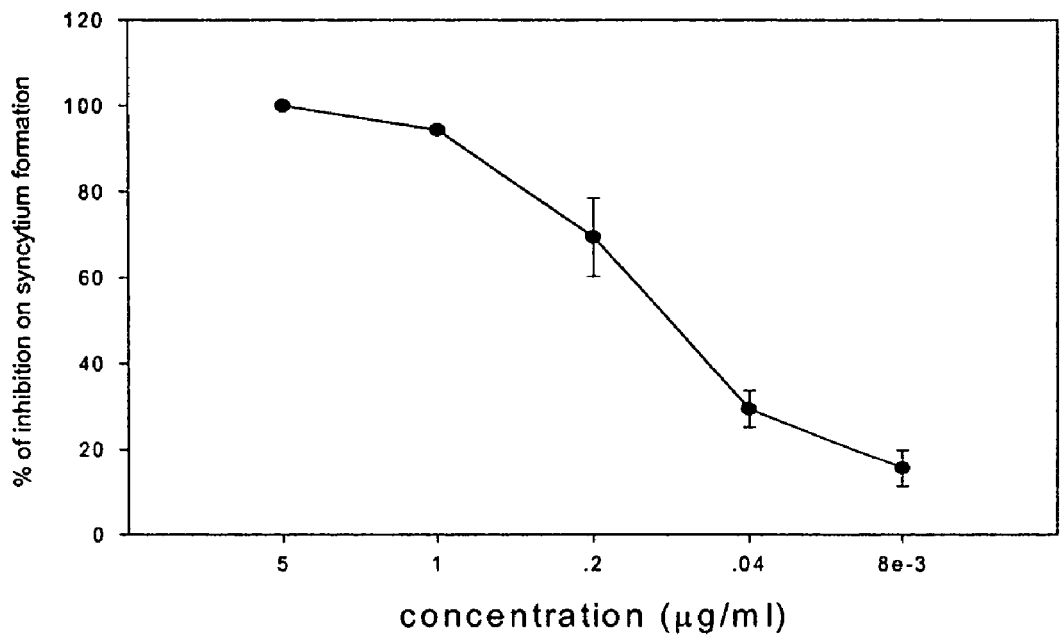
FIG. 6 Inhibition of AZT on cytopathic effect (CPE) of HIV-1 ($EC_{50}$ is 0.092 μg/ml)

The Cytopathic Effect (CPE) Inhibition Assay of Concentricolide A on HIV-I Infected C8166 Cells To 100 μl of a culture medium containing corresponding concentration of concentricolide A from example 1 were added C8166 cells ($4\times10^5$/ml) and HIV-$1_{IIIB}$ at a multiplicity of infection (M.O.I) of 0.06. The final volume was 200 μl. AZT was used as positive drug control. The plates were incubated in a humidified incubator at 37° C. and 5% $CO_2$. After 3 days of culture, the cytopathic effect was measured by counting the number of syncytia in each well under an inverted microscope. $EC_{50}$ (50% Effective Concentration) was the compound concentration inhibiting 50% of syncytia formation. The cytopathic effect (CPE) inhibition %=(1-number of $syncytia_{exp}$/number of $syncytia_{control}$)×100. The results were as shown in FIGS. 5 and 6.

CONCLUSION

The data demonstrated that concentricolide exhibits low cytotoxicity and good activity against HIV-1 in vitro. The selected index (S.I.) is 222. The target site of concentricolide probably is binding and fusion between HIV and cell. So, as a small molecule compound that blocks the binding and fusion between HIV and cell, concentricolide A has great significance.

The invention claimed is:

1. Compounds of the general formula (I) and pharmaceutically acceptable salts, and stereoisomers thereof:

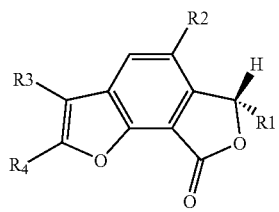

(I)

in which

R1 represents $C_1$-$C_4$ alkyl;

R2 represents H, halogen, —OH, NRR' or —$NO_2$, wherein R and R' represent H or $C_1$-$C_4$ alkyl R3 represents H, halogen, —OH, NRR' or —$NO_2$, wherein R and R' represent H or $C_1$-$C_4$ alkyl;

R4 represents H, halogen or —$NO_2$.

2. Compounds according to claim 1, selected from the compounds represented by the following formula:

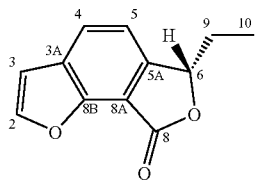

(II)

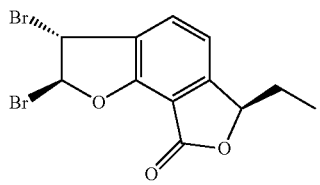

B1

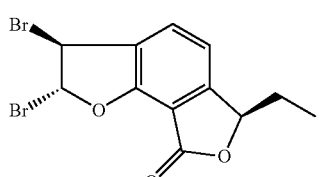

B2

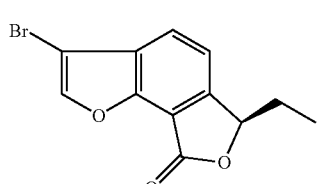

C

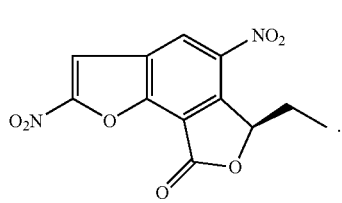

D

3. Compounds according to claim 1, selected from the compounds represented by the following formula (II):

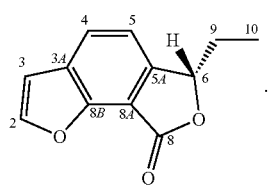 (II)

4. An extract comprising the compound of formula (II):

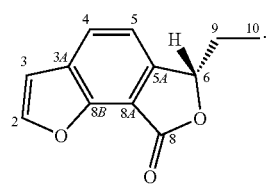 (II).

5. A pharmaceutical composition comprising the compounds according to any one of claims 1-3 or pharmaceutically acceptable salts, stereoisomers, hydrates, or solvates thereof, or the extract as claimed in claim 4, and a pharmaceutically acceptable carrier or excipient.

6. Process for preparing the compounds of formula (I), comprising:
   a) extracting fruit bodies of *Daldinia* concentrica of Yunnan or their fermented liquid with an organic solvent;
   b) isolating the extract from a) by silica gel chromatographic to give the compound of the formula (II):

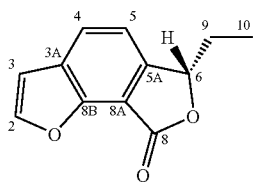 (II)

c) subjecting the compound of formula (II) to bromination, nitration and alkylation to give the compound of the formula (I).

7. A composition according to claim 5, wherein said compound is selected from

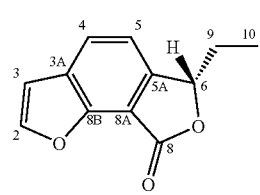 (II)

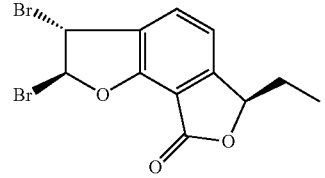 B1

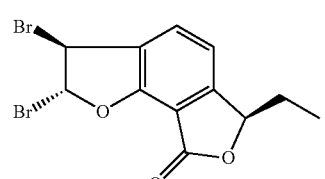 B2

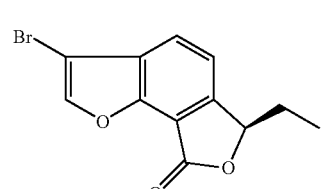 C

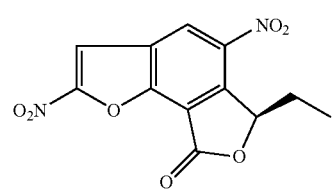 D

8. A method for treatment of HIV infection in a patient, comprising administrating the compounds according to any one of claims 1-3, wherein the compounds blocks the binding and fusion between HIV and HIV uninfected CD4 cells, thereby treating HIV infection in the patient.

\* \* \* \* \*

UNITED STATES PATENT AND TRADEMARK OFFICE
CERTIFICATE OF CORRECTION

PATENT NO.        : 7,659,308 B2                                        Page 1 of 1
APPLICATION NO.   : 10/576758
DATED             : February 9, 2010
INVENTOR(S)       : Jikai Liu et al.

It is certified that error appears in the above-identified patent and that said Letters Patent is hereby corrected as shown below:

On the Title Page Item 87
"PCT Pub. No.: WO2005/137841" should read --PCT Pub. No.: WO2005/037841--.

Signed and Sealed this

Second Day of November, 2010

David J. Kappos
*Director of the United States Patent and Trademark Office*